United States Patent [19]
Dziewiszek et al.

[11] Patent Number: 5,977,327
[45] Date of Patent: Nov. 2, 1999

[54] SYNTHESIS OF ANNAMYCIN

[75] Inventors: Krzysztof Dziewiszek, The Woodlands; Waldemar Priebe, Houston, both of Tex.

[73] Assignee: Board of Regents, The University of Texas System, Austin, Tex.

[21] Appl. No.: 08/898,618

[22] Filed: Jul. 22, 1997

Related U.S. Application Data

[60] Provisional application No. 60/022,585, Jul. 23, 1996.
[51] Int. Cl.[6] .............................. C07H 1/00; C07H 15/27
[52] U.S. Cl. ............................................ 536/6.4; 536/18.5
[58] Field of Search ....................................... 536/6.4, 18.5

[56] References Cited

U.S. PATENT DOCUMENTS 4,537,882  8/1985  Horton et al. ............................. 514/34

*Primary Examiner*—Elli Peselev
*Attorney, Agent, or Firm*—Arnold, White & Durkee

[57] ABSTRACT

An improved method for synthesis of Annamycin is described. The synthesis relies upon a method of selectively deacetylating the Annamycin precursor and purification of the deacetylated product by a filtration step. In addition, the method includes an improved method for desilylating the Annamycin precursor that utilizes acidic conditions. Lastly, improved purification methods of the final Annamycin product are disclosed.

13 Claims, 2 Drawing Sheets

SYNTHESIS OF ANNAMYCIN

CROSS-REFERENCE TO RELATED APPLICATIONS

This application relies for priority on the provisional application entitled Improvements in the Synthesis of Annamycin, this application was filed on Jul. 23, 1996 and has Ser. No. 60/022,585. That provisional application is specifically incorporated herein by reference.

STATEMENT REGARDING FEDERALLY SPONSORED RESEARCH OR DEVELOPMENT

Research leading to this invention was federally supported, in part, by a grant from the U.S. Government, Grant No. CA 55320. The U.S. government has certain rights thereunder in this invention.

BACKGROUND OF THE INVENTION

Anthracycline antibiotics such as doxorubicin and daunorubicin are among the most potent and clinically important antineoplastons. However, their toxicity interferes with their therapeutic use against human malignancy. In addition, tumor cells develop resistance to these antibiotics after repeated treatments. This characteristic of tumor cells is known as multidrug resistance (MDR).

Although a variety of biological mechanisms give rise to MDR, it is usually caused by the overexpression of P-glycoprotein, which is believed to be involved in causing the efflux of drugs from cells, including cancer cells. This mechanism affects not only anthracycline antibiotics but many structurally unrelated anticancer drugs as well.

Theoretically, at least two approaches may be used to avoid MDR. The first approach is to use therapeutics that suppress the expression of P-glycoprotein. Unfortunately, this approach has met with little success. A second approach is to identify cancer therapeutics that do not cause overexpression of P-glycoprotein. Annamycin is one such drug.

Annamycin is an anthracycline derivative that has been proven by in vitro and in vivo studies to have low cardiotoxicity and it does not cause MDR. Even though it does not exhibit MDR, Annamycin's potential as an effective cancer therapeutic has been limited by the lack of a method for producing the drug in pure form or in sufficient quantities for therapeutic use. Known methods of synthesis are technically difficult and cannot be scaled up. Furthermore, the yield of Annamycin that is produced by known synthetic methods is unsatisfactory. See Horton et al., 1984; U.S. Pat. No. 4,537,882.

Using the procedure of Horton et al., 1984 and U.S. Pat. No. 4,537,882, which are specifically incorporated herein by reference, the overall yield of Annamycin from the starting material, 4-demethoxydaunomycinone, is at most, 3%. When the Horton procedure is scaled up, yields are frequently as low as 2%, even when enantiomerically pure starting materials are used. Furthermore, the purity of the final product is only about 80%. These preparations are too impure for therapeutic use, which requires higher purity and detailed knowledge concerning the nature of impurities.

In the procedure of Horton et al. (1984) silylated Annamycin precursor is prepared by the condensation of silylated adriamycinone derivative with 3,4-di-O-acetyl-L-rhamnal. This reaction gives a mixture of two products, one having the undesirable gluco configuration and the other having the desired manno configuration.

In the Horton procedure the reaction product having the manno configuration must be purified away from the gluco form. This is a difficult separation because the two compounds have similar polarities. To separate the compounds, a silica column having a mass that is 100 times that of the sample is required. In addition, the polarity of solvent required to elute the desired product is low. This further reduces the recovery of product from the column. Thus, more than half of the Annamycin precursor is lost because of irreversible adsorption to the silica. Furthermore, silica columns do not completely resolve the manno and gluco species and almost half of the product collected is collected as a mixture of the gluco and manno species.

In the end, the Horton method requires 16 grams (g) of protected adriamycinone derivative, a 5 kilogram (kg) silica gel column and 200 liters (L) of solvent (a toluene/acetone (99.3/0.7) mixture) to produce just 9 g of the silylated 3,4-di-O-acetyl-L-manno adriamycinone intermediate. In the process, about 7 g of the mixed gluco and manno forms is obtained and chromatography of this mixture must be repeated. Ultimately, the overall product yield in this synthetic step ranges from 16% to 40%. In addition to the unacceptably low yields, it is clear that this procedure cannot be scaled up to produce the quantities of Annamycin required for therapeutic use.

Another inefficient step in the synthesis of Annamycin is the step for removing the silyl protecting group from the silylated Annamycin intermediate. In the Horton method, this protecting group is removed by treating the purified manno intermediate with tetrabutylammonium fluoride in a pyridine/THF solution. However, the basic lability of the anthracyclines substantially reduces the yield of product from this reaction and the Annamycin obtained is generally no more than 80% pure.

Yields are decreased further during purification. Recoveries from the silica column used in the final purification are low because Annamycin is highly polar and poorly soluble. The overall yield of the purified product in this step is between 10–15%, which also is too low for commercial viability.

New synthetic methods are needed that can be used to produce Annamycin to a purity of over 95% and in a relatively high yield. To accomplish this, improved methods for preparing the pure silyl derivative of Annamycin are needed. In addition, improved methods for removing the silyl protecting group from the silylated Annamycin precursor that leave the molecule intact are needed, as are improvements to methods for purifying the Annamycin product after the desilylation reaction. A method that includes these improvements could be used to produce large quantities of Annamycin in a sufficient purity for therapeutic use.

BRIEF SUMMARY OF THE INVENTION

The present invention relates to new synthetic methods that can be used to produce Annamycin to a purity of over 95% and in a relatively high yield. The invention provides more efficient methods for the preparation of the silyl derivative of Annamycin. New and improved methods for removing the silyl protecting group on the Annamycin precursor that leave the molecule intact and a new and more efficient method for purifying the finished Annamycin product are also disclosed. These new methods can be conveniently scaled up to produce large quantities of Annamycin of a sufficient purity for therapeutic use.

In FIG. 1 is shown the first four reaction steps of the Annamycin synthetic scheme of the present invention. The name for of each numbered compounds is provided in Table 1 below. These reactions result in the synthesis of the silylated α-manno adriamycianone intermediate (7) along with the β-gluco adriamycinone isomer (6). More specifically, silylated adriamycinone (4) is prepared by standard methods well known to those of skill in the art. Horton et al. 1984. This compound is reacted with 3,4-di-O-acetyl-L-rhamnal in reaction "b" to prepare compound (7) along with the β-gluco side product (6).

TABLE 1

Compound Nomenclature

| Compound # | Name | Chemical Abstract Name | CAS # |
|---|---|---|---|
| 1 | (+)-4-demethoxy-daunomycinone | (7S-cis)-9-acetyl-7,8,9,10-tetrahydro-6,7,9,11-tetrahydroxy-5,12-Naphtacenedione | 60660-75-5 |
| 2 | (+)-14-Bromo-4-demethoxy-daunomycinone | (7S-cis)-9-(bromoacetyl)-7,8,9,10-tetrahydro-6,7,9,11-tetrahydroxy-5,12-Naphtacenedione | 99570-80-6 |
| 3 | (+)-4-Demethoxy-adriamycinone; 1-Demethoxy-adriamycinone | (7S-cis)-7,8,9,10-tetrahydro-6,7,9,11-tetrahydroxy--9-(hydroxyacetyl)-5,12-Naphtacenedione | 86333-80-4 |
| 4 | (+)-4-Demethoxy-14-O-tert-butyldimethylsilyladriamycinone | (7S-cis)-9-[[[(1,1-dimethylethyl)dimethylsilyl]oxy]acetyl]-7,8,9,10-tetrahydro-6,7,9,11-tetrahydroxy-5,12-Naphtacenedione | 130195-68-5 |
| 5 | 3,4-Di-O-acetyl-L-rhamnal |  | 34819-86-8 |
| 6 | (+)-4-Demethoxy-14-O-tert-butyldimethylsilyl-7-O-(3,4-di-O-acetyl-2,6-dideoxy-2-iodo-α-L-gluco-pyranosyl)adriamycinone | (7S-cis)-7-[(3,4-di-O-acetyl-2,6-dideoxy-2-iodo-α-L-glucopyranosyl)oxy]-9-[[[(1,1-dimethylethyl)dimethylsilyl]-oxy]acetyl]-7,8,9,10-tetrahydro-6,9,11-trihydroxy-5,12-Naphtacenedione |  |
| 7 | (+)-4-Demethoxy-14-O-tert-butyl-dimethylsilyl-7-O-(3,4-di-O-acetyl-2,6-dideoxy-2-iodo-α-L-mannopyrano-syl)adria-mycinone | (7S-cis)-7-[(3,4-di-O-acetyl-2,6-dideoxy-2-iodo-α-L-mannopyranosyl)oxy]-9-[[[(1,1-dimethylethyl)dimethylsilyl]-oxy]acetyl]-7,8,9,10-tetrahydro-6,9,11-trihydroxy--5,12-Naphtacenedione | 92761-44-9 |
| 8 | (+)-4-Demethoxy-14-O-tert-butyldimethylsilyl-7-O-(2,6-dideoxy-2-iodo-α-L-mannopyranosyl) adriamycinone (AmP 28) | (7S-cis)-7-[(2,6-dideoxy-2-iodo-α-L-mannopyranosyl)oxy]-9-[[[(1,1-dimethyl-ethyl)dimethylsilyl]oxy]acetyl]-7,8,9,10-tetrahydro-6,9,11-trihydroxy--5,12-Naphtacenedione | 92689-48-0 |
| Anna-my-cin | (+)-4-Demethoxy-7-O-(2,6-dideoxy-2-iodo-α-L-mannopyranosyl) adriamycinone | (7S-cis)-7-[(2,6-dideoxy-2-iodo-α-L-mannopyranosyl)oxy]-7,8,9,-10-tetrahydro-6,9,11-trihy-droxy-9-(hydroxyacetyl)--5,12-Naphtacenedione | 92689-49-1 |

The present invention also relates to novel methods for deacetylating compound (7) to form silylated Annamycin precursor compound (8). The present methods produce this precursor selectively by deacetylating only the α-manno Annamycin intermediate (7) leaving the gluco form, compound (6), in the acetylated state.

These methods resulted from the inventors discovery that under certain conditions the reaction for deacetylating compounds (6) and (7), occurred at greatly different rates. For example, when subjected to the Zemplen reaction in methanol, the β-gluco compound (6) reacted slowly or decomposed, whereas deacetylation of the α-manno isomer (7) proceeded rapidly to produce the desired silylated Annamycin reaction product (8) with yields in the range of 80–90%. Further refinement of this reaction, to the conditions described in Example I, allowed the selective deacetylation of the α-manno compound (7) without any discernable deacetylation of the β-gluco compound (6), as evidenced by the thin layer chromatographic analysis. The preferred reaction solvent for the selective deacetylation reaction of the method is a solution of dichloromethane and ethanol, as also described in Example I.

As shown in FIG. 2, the deacetylation product mixtures of the present method, includes the acetylated β-gluco Annamycin isomer and the silylated Annamycin precursor compound (8). These products have such distinct polarities that a simple silica gel filtration step can be used to purify compound (8). The filtration method of purification is vastly superior to the complex and inefficient silica chromatography step used in prior methods. For example, in the present invention only 200 g of silica gel and 10 L of a 95:5 toluene/acetone mixture are required to produce 9 g of silylated Annamycin precursor (8). Furthermore, only 10 g of compound (4) is required. To produce the same amount of compound (8) by prior methods would require 16 g of compound (4), 5 kg of silica, and 200 L of solvent. As a result, the deacetylation procedure of the present invention can be scaled up to produce large quantities of Annamycin.

Alternatively, the difference in polarity between compounds (6) and (8) is large enough to allow their separation by precipitation. In this method reaction products (6) and (8) are dissolved in a minimum amount of THF and an equal volume of dichloromethane is added. This solution is diluted by 9-fold in hexane/ethyl ether (7:3) to precipitate compound (8) and the subsequent precipitation is carried out, similarly, with THF/dichloromethane followed by a 9-fold dilution with hexane.

The present invention also relates to improvements in the desilylation and purification of the final Annamycin reaction product. Surprisingly, the inventors discovered that t-butyldimethylsilyl groups could be removed from the Annamycin precursor in acid with no hydrolysis of the glycosidic bond. Previously, desilylation was effected by treatment under basic conditions with tetrabutylammonium fluoride rather than under acidic conditions to avoid hydrolysis of the glycosidic bond. The acid lability of silyl protection groups coupled with the stabilized glycosidic bond facilitated the use of low pH for t-butyldimethylsilane removal. For example, desilylation reactions of compound (8) have been successfully carried out in water miscible solvents like dimethylsulfoxide (DMSO), dimethyl formamide (DMF), 1,4-dioxane, methanol, acetone and mixtures of these solvents with the addition of 1 N acid, such as HCl or $H_2SO_4$. These treatments can be used to produce Annamycin in much higher yields than the fluoride-mediated deprotection used in previous methods.

In the present method, the preferred solvent for desilylation of compound (8) is tetrahydrofuran (THF). The inventors discovered that in THF the desilylation reaction required the addition of an equal volume of 1 N hydrochloric acid. Under these conditions, the desilylated Annamycin product precipitated from the mixture as an Annamycin/THF complex. Surprisingly, other isomers, such as the β-gluco-isomer, do not form complexes with THF and do not precipitate under these same conditions. Thus, collection of the precipitated Annamycin reaction product immediately after the reaction provides a convenient method for obtaining highly purified product. The product collected in this manner is approximately 95% pure. This compares with an 80% purity of Annamycin product produced by known methods.

The present invention also relates to steps for further purifying the Annamycin product. As shown in FIG. 3, the method requires redissolving the precipitated product in THF and reprecipitating the Annamycin by adding hexane. This is followed by redissolving the residue in THF and precipitating it with toluene after evaporating half of the THF and finally precipitating the Annamycin from THF with water with the THF evaporation step. More preferred is the following precipitation method: a first precipitation from THF after adding hexane/diethylether (7:3), followed by precipitation from THF after mix with hexane, and a final precipitation from THF after mixing with water, as described in Example II. The Annamycin produced in this manner is over 98% pure and is produced with a relatively high yield of approximately 59%, as described in Example II.

DETAILED DESCRIPTION OF THE INVENTION

The following examples are offered by way of illustration and are not intended to limit the invention in any manner. In the examples, all temperatures are in degrees Celsius and all percentages are by weight for solids and volume if for liquids, unless otherwise noted.

In the examples that follow, thin layer chromatography (TLC) was performed on silica gel 60 F-254 (E. Merck AG, Darmstadt, West Germany) precoated sheets (0.2 mm). Column chromatography was with E. Merck silica gel 60, 230–400 mesh ASTM. Unless stated otherwise, 400-MHz $^1$H NMR spectra were obtained in $CDCl_3$ solution using an internal standard of $Me_4Si$ on a Bruker-400-MHz spectrometer. 100-MHz $^{13}$C NMR spectra were obtained in DMSO-$d_6$ solution with an internal standard of DMSO on a Bruker-400-MHz spectrometer. All products obtained in Examples III–VII compare favorably with Annamycin obtained in the preferred desilylation reaction employing THF and 1N HCl, purified and characterized as a standard.

EXAMPLE I

SYNTHESIS OF (+)-4-DEMETHOXY-14-O-TERT-BUTYL DIMETHYLSILYL-7-O-(2,6-DIDEOXY-2-IODO-α-L-MANNOPYRANOSYL) ADRIAMYCINONE (8)

Figure 1:
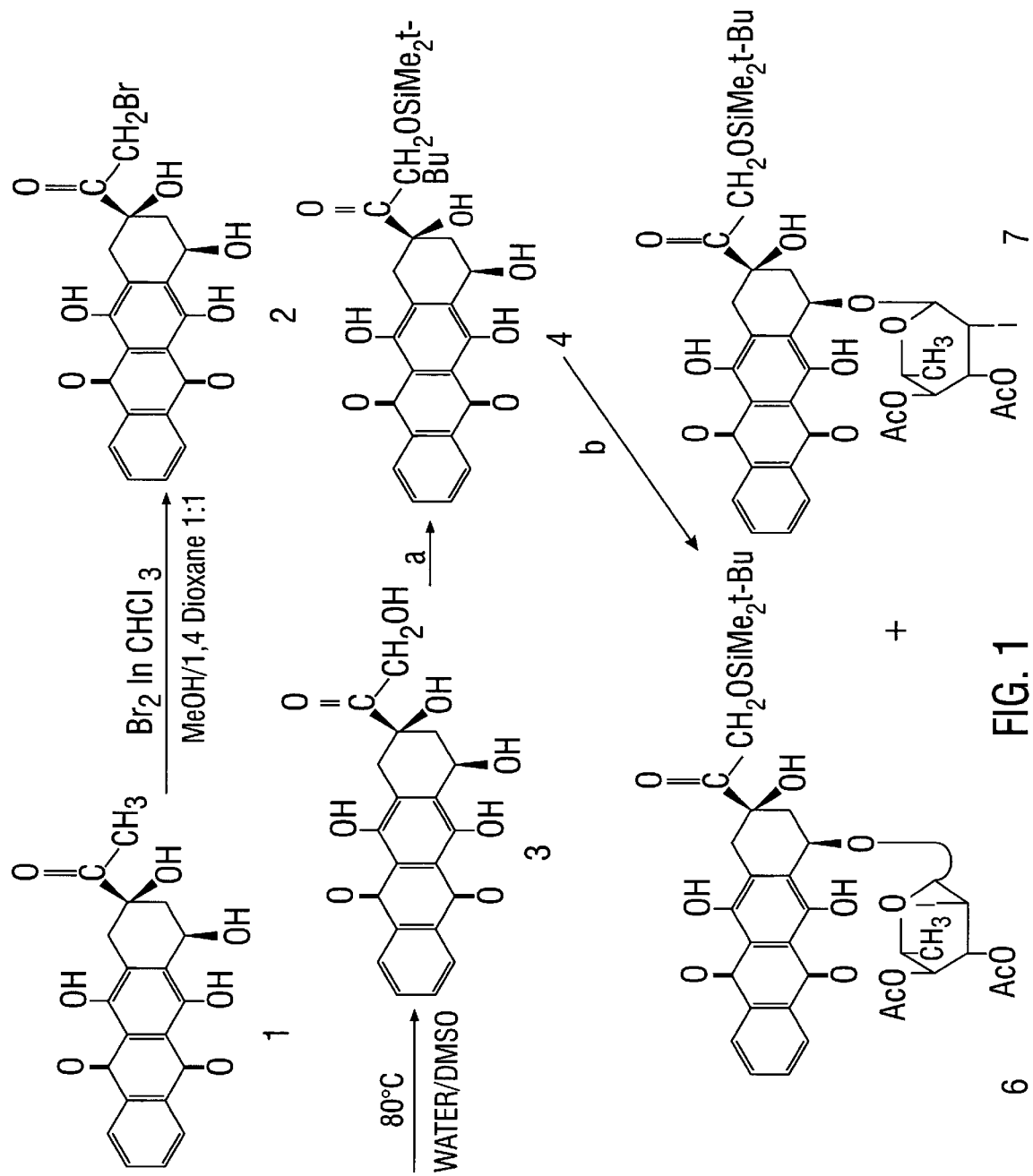
FIG. 1 A flow diagram of the synthetic scheme for fully protected Annamycin precursor.
Figure 2:
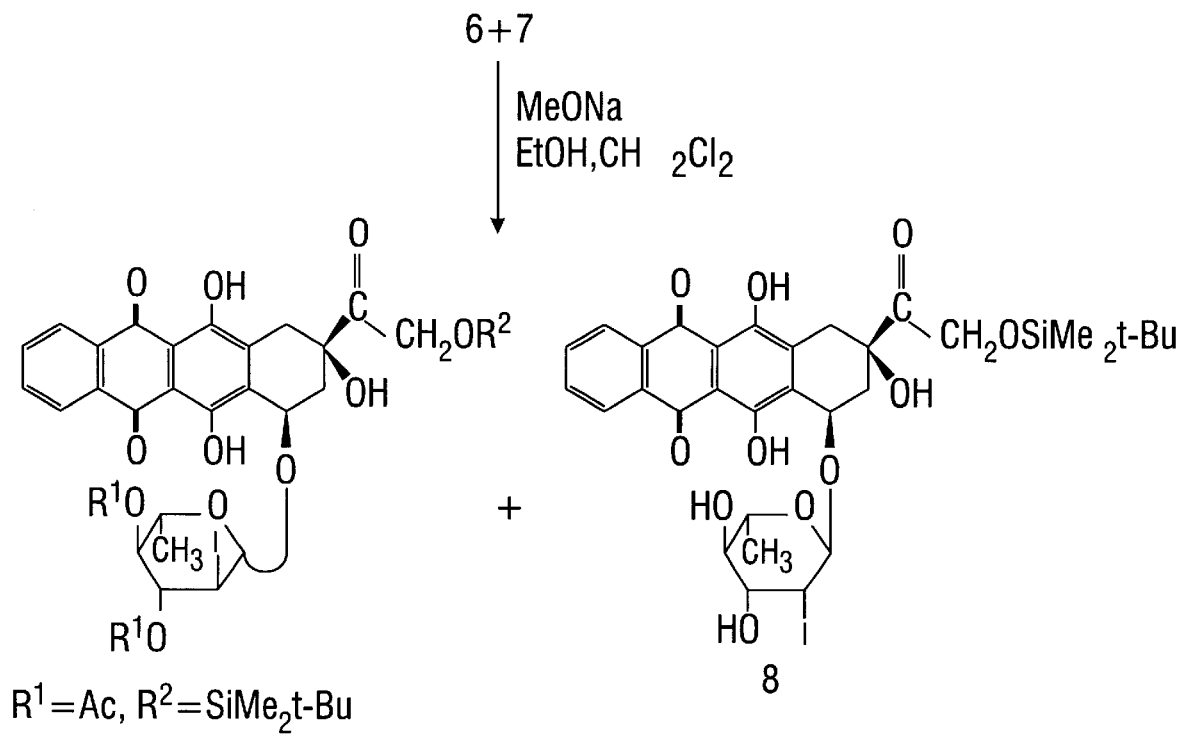
FIG. 2 A flow diagram of the synthetic scheme of Annamycin from its fully protected precursor.
Figure 3:
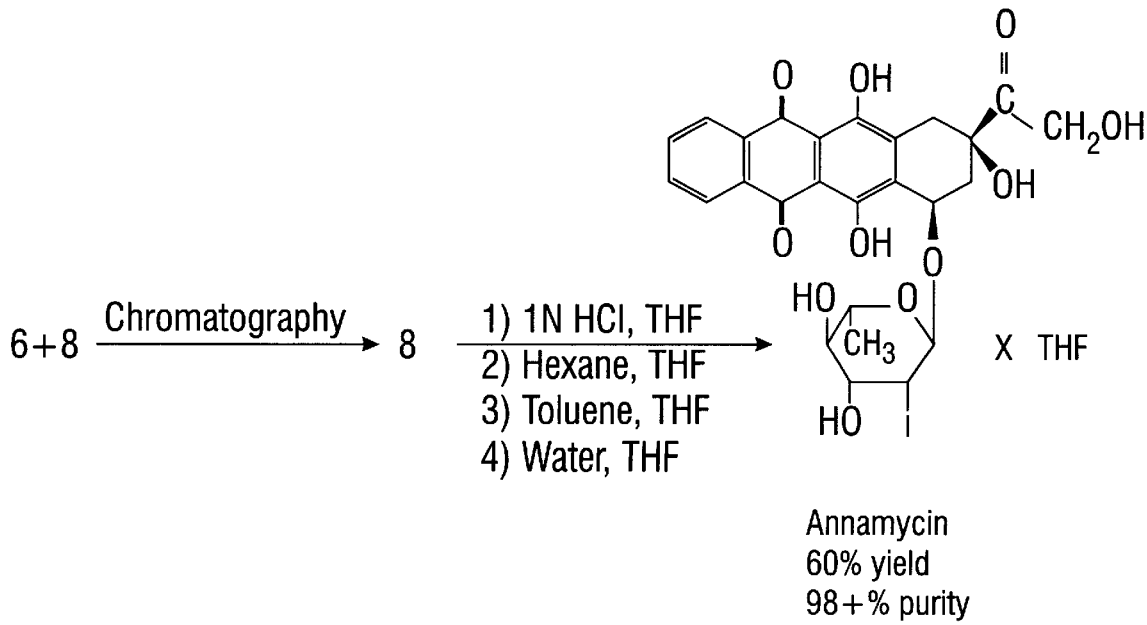
FIG. 3 A diagram showing the purification steps for obtaining the final purified Annamycin product after deprotection.

To a solution consisting of a mixture of compounds (6) and (7), shown in FIG. 1, (1.8530 g, 2.21 mmol) in $CH_2Cl_2$ (48 mL) and EtOH (16 mL), a 1N MeONa solution in MeOH (1.6 mL) was added at room temperature with stirring. Next 1.6 mL of a 1N MeONa solution in MeOH (1.6 mL) was added after 50 min. After 1.5 hr. the reaction was checked by TLC developed with $CCl_4$/MeOH (96:4), and the reaction mixture was diluted with dichloromethane (300 mL) and 0.05N HCL (100 mL) was added. The resulting mixture was shaken in a separatory funnel and, after separation, the organic layer was washed with water (2×50 mL), dried over $Na_2SO_4$, filtered and evaporated. The residue left after evaporation was precipitated from 4 mL of $CH_2Cl_2$ by addition of 35 mL of hexane. The precipitate was filtered, washed with hexane (40 mL) and then dried in vacuo (11 mbar) at ambient temperature for 30 min. to give crude product (8) (1.3618 g, 82%). The crude product was then filtered through silica with a solution of 95:5 toluene/acetone and precipitated from $CH_2Cl_2$ by addition of hexane. Product was then dried in vacuo (11 mbar) at ambient temperature for 30 minutes to give pure compound (8) (1.358 g; 55%): $^1$H NMR d 0.15 (s, 6H, $Me_2Si$), 0.95 (s, 9H, $CMe_3$), 1.40 (d, 3H, $J_{6',5'}$=6.2 Hz, H-6'), 2.18 (dd, 1H, $J_{8a,7}$=4.4 Hz, $J_{8a,8e}$=15.0 Hz, H-8a), 2.35 (d, 1H, $J_{8e,8a}$=14.9 Hz, H-8e), 2.85 (dd, 1H, $J_{3',2'}$=4.0 Hz, $J_{3',4'}$=8.9 Hz, H-3'), 3.02 (d, 1H, $J_{10a,10e}$=19.0 Hz, H-10a), 3.24 (d, 1H, $J_{10e,10a}$=19.0 Hz, H-10e), 3.58 (t, 1H, SJ=18.2 Hz, H-4'), 3.94 (m, 1H, H-5'), 4.18 (s, 1H, 9OH), 4.54 (d, 1H, $J_{2',3'}$=3.9 Hz, H-2') 4.84, 4.90 (2d, 2H, H-14), 5.22 (bs, 1H, H-7), 5.75 (s, 1H, H-1'), 7.9, 8.4 (2m, 4H, H-1,2,3,4).

EXAMPLE II

DESILYLATION IN THF/HCl

To a solution of compound (8), (16.5928 g, 21.99 mmol) in THF (415 mL), 1N HCl (415 mL), was added. After 25 minutes the progress of the reaction was checked by TLC developed in toluene/acetone (6:4 or 5:1) and half of the THF was evaporated in vacuo at 20° C. (35 mbar). The precipitate was filtered off and washed with water until the pH reached neutral (14×40 mL), then washed with ether ($Et_2O$, 5×32 mL) and subsequently with water (3×40 mL). The crude product was pre-dried on a Buchner funnel and then dried in vacuo (0.08 mbar) at room temperature for 38 hrs.

EXAMPLE III

DESILYLATION IN METHANOL/HCl

To a solution/suspension of compound (8) (1.0064 g, 1.33 mmol) in methanol (45 mL), 1N HCl (10 mL) was added. The progress of the reaction was monitored by TLC developed in toluene/acetone, 6:4 and chloroform/methanol, 94:6. After 45 min. 5 mL of 1N HCl solution was added to the reaction mixture. After 1 hr. 15 min. the product of the reaction was precipitated by addition of 30 mL water and filtered off. Product was washed with water until neutral pH (4×10 mL), diethylether (3×10 mL) and again with water (2×10 mL). Crude product was pre-dried on Buchner funnel and then dried in vacuo (0.1 mbar) at room temperature for 24 hrs. to give 0.6722 g (79% yield) of deep red powder.

EXAMPLE IV

DESILYLATION IN METHANOL/$H_2SO_4$

To a solution/suspension of compound (8) (1.0065 g, 1.33 mmol) in methanol (45 mL), 10 mL of 1N $H_2SO_4$ was added. The progress of the reaction was monitored by TLC developed in toluene/acetone, 6:4 and chloroforn/methanol, 94:6. After 15 min. the product of the reaction was precipitated by adding 35 mL of water and filtered off. Product was washed with water until neutral pH (4×10 mL), diethylethe (3×10 mL) and again with water (2×10 mL). Crude product was pre-dried on Buchner funnel and then dried in vacuo (0.1 mbar) at room temperature for 24 hrs. to give 0.6318 g (74% yield) of deep red powder.

EXAMPLE V

DESILYLATION IN ACETONE/H₂SO₄

To a solution of compound (8) (0.7592 g, 1.01 mmol) in acetone (30 mL) 3.5 mL 1N $H_2SO_4$ was added. The progress of the reaction was monitored by TLC developed in toluene/acetone, 6:4 and chlorofron/methanol, 94:6. After 1 hr. the product of the reaction was precipitated by addition of 35 mL water and filtered off. The product was washed with water until neutral pH (4×10 mL), diethyleher (3×10 mL) and again with water (2×10 mL). Crude product was pre-dried on Buchner funnel and then dried in vacuo (0.1 mbar) at room temperature for 48 hrs. to give 0.4994 g (77% yield) of deep red powder.

EXAMPLE VI

DESILYLATION IN DMSO/HCl

To a solution of compound (8) (0.7815 g, 1.04 mmol) in DMSO (30 mL) 7.5 mL of 1N HCl was added. Progress of the reaction was monitored by TLC developed in toluene/acetone, 6:4 and chloroform/methanol, 94:6. After 1 hr. 20 min. the product of the reaction was precipitated by addition of water (37 mL) and filtered off. The product was washed with water until neutral pH (4×10 mL), dietheylether (3×10 mL) and again with water (2×10 mL). Crude product was pre-dried on Buchner funnel and then dried in vacuo (0.1 mbar) at room temperature for 48 hrs. to give 0.5165 g (78% yield) of deep red powder.

EXAMPLE VII

DESILYLATION IN DMSO/H₂SO₄

To a solution of compound (8) (0.7613 g, 1.01 mmol) in DMSO (5 mL) and ethanol (10 mL) 1 mL of 1N $H_2SO_4$ was added. Progress of the reaction was monitored by TLC developed in toluene/acetone, 6:4 and chloroform/methanol, 94:6. After 1 hr. 10 min. product of the reaction was precipitated by addition of water (15 mL) and filtered off. Product was washed with water until neutral pH (4×10 mL), diethylether (3×10 mL) and again with water (2×10 mL). Crude product was pre-dried on Buchner funnel and then dried in vacuo (0.1 mbar) at room temperature for 48 hrs. to give 0.5338 g (83% yield) of deep red powder.

EXAMPLE VIII

PURIFICATION OF ANNAMYCIN

Crude product was purified further by triple precipitation from THF. To accomplish this, approximately 87 mL of THF was used to redissolve each gram of Annamycin product and an equal volume of one of the following solvents was added to precipitate the Annamycin in each successive precipitation step. In the preferred method, the first precipitation was accomplished by adding an equal volume of a 7:3 mixture of hexane\diethylether, the second precipitation was accomplished by the addition of an equal volume of hexane, and the third precipitation was by addition of an equal volume of water and evaporation of half of the THF. Product obtained in this way (9.0146 g; 59%) was a complex containing 3 molecules of Annamycin per 2 molecules of THF and its purity by HPLC analysis was better than 98%. HPLC analysis was on an analytical C-18 reverse phase column with increasing concentrations of methanol/acetonitrile in water. The purity was determined by measuring the area of the absorbance peaks. $^1$H NMR (DMSO-d6) d 1.20 (d, 3H, $J_{6',5'}$=6.2 Hz, H-6'), 1.75 (m, 2.7H, Ha from THF), 2.10 (dd, 1H, $J_{8a,7}$=5.6 Hz, $J_{8a,8e}$=14.5 Hz, H-8a), 2.18 (dd, 1H, $J_{8e,8a}$=14.8 Hz, $J_{8e,7}$=2.9 Hz, H-8e), 250 (DMSO peak), 2.75 (dd, 1H, $J_{3',2'}$=3.9 Hz, $J_{3',4'}$=8.8 Hz, H-3'), 2.95 (d, 1H, $J_{10a,10e}$=18.4 Hz, H-10a), 3.00 (d, 1H, $J_{10e,10a}$=18.4 Hz, H-10e), 3.20 (t, 1H, SJ=18.1 Hz, H-4'), 3.59 (m, 2.7H, Hb from THF), 3.95 (m, 1H, H-5'), 4.30 (d, 1H, $J_{2',3'}$=4.0 Hz, H-2'), 4.55 (s, 2H, H-14), 4.89 (t, 1H, exchangeable, OH), 4.92 (m, 1H, H-7), 5.18 (d, 1H, exchangeable, OH), 5.38 (d, 1H, exchangeable, OH), 5.49 (s, 1H, H-1'), 5.50 (d, 1H, exchangeable, OH), 7.9, 8.4 (2m, 4H,H-1,2,3,4); $^{13}$C NMR (DMSO-d6) d 17.0(s, 1C, C-6'), 24.5 (s, 1C, THFb), 31.7 (s, 1C, C-2'), 31.9 (s, 1C, C-10), 36.4 (s, 1C, C-8), 63.0 (s, 1C, C-3'), 66.4 (s, 1C, C-5'), 67.4 (s, 1C, THFa), 69.4, $^{13}$C-NMR (DMSO-d6) δ 17.9 (s, 1C, C-6'), 25.1 (s, 1C, THFb), 40.6, 36.6, 32.1 (3s, 3C, C-2',8,10), 63.6 (s, 1C, C-14), 67.0, 67.5, 70.4, 69.7 (4s, 4C, C-7, 5', 3', THFa), 74.2, 74.7 (2s, 2C, C-9, 4'), 104.5 (s, 1C, C-1'), 110.1, 110.8 (2s, 1C, C-11a, 5a), 126.6, 132.6, 132.8, 134.4, 135.1, 135.0, 136.0 (7s, 8C, C-2, 3, 1, 4, 4a, 12a, 10a), 136.0 (s, 1C, C-6a), 155.1, 156.4 (2s, 2C, C-6, 11), 186.2, 186.3 (2s, 2C, C-5, 12), 214 (s, 1C, C-13).

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, compounds that are chemically analogous to iodine may be substituted into the 2' position of the sugar ring, silyl groups other than t-butyldimethylsilane may be used to silylate Annamycin intermediate and acyl groups other than acetyl groups may be used to protect Annamycin precursors. All such modifications are intended to be included within the scope of the appended claims.

REFERENCES CITED

The following references to the extent that they provide procedural details supplementary to those set forth herein, are specifically incorporated herein by reference.

REFERENCES

Horton, D.; Priebe, W.; Varela, O., (1984) *Carbohydrate Res.* 130, c1–c3.

Horton, D.; Priebe, W., (1985) U.S. Pat. No. 4,537,882.

What is claimed is:

1. A method for synthesizing Annamycin comprising mixing (7S-cis)-7-[(2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, compound (8), with a solvent and an acid in a reaction mixture that desilylates (7S-cis)-7-[(2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, compound (8), to produce Annamycin.

2. The method for synthesizing Annamycin of claim 1 wherein said acid is HCl.

3. The method for synthesizing Annamycin of claim 1 wherein said solvent is selected from the group consisting of tetrahydrofuran, methanol, acetone, dimethylsulfoxide and a mixture of 1 volume dimethyl sulfoxide with 2 volumes of ethanol.

4. The method for synthesizing Annamycin of claim 1 wherein said solvent is tetrahydrofuran.

5. The method for synthesizing Annamycin of claim 1 wherein said (7S-cis)-7-[(2,6-dideoxy-2-iodo-α-L- mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione, compound (8), is prepared by reacting a mixture of (7S-cis)-7-[(3,4-di-O-acetyl-2,6-dideoxy-2-iodo-β-L-glycopyranosyl)oxy]-9-[[[(1,1-dimethylethyl)dimethylsilyl]oxy]acetyl]-7,8,9,10-tetrahydro-6,9,11-trihydroxy-5,12-Napthacenedione compound (6) and (7S-cis)-7-[(3,4-di-O-acetyl-2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione compound (7) in a deacylation reaction mixture that selectively deacylates (7S-cis)-7-[(3,4-di-O-acetyl-2,6-dideoxy-2-iodo-α-L-mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione compound (7) to form said (7S-cis)-7-[(2,6-dideoxy-2-iodo-α-L-mannopyranosyl) oxy]-9-[[[(1,1-dimethylethyl)dimethylsilyl]oxy]acetyl]-7,8,9,10-tetrahydro-6,9,11-trihydroxy-5,12-Napthacenedione, compound (8).

6. The method for synthesizing Annamycin of claim 5 wherein said (7S-cis)-7-[(2,6-dideoxy-2-iodo-α-L-mannopyranosyl)oxy]-9[[[(1,1-dimethylethyl) dimethylsilyl]oxy]acetyl]-7,8,9,10-tetrahydro-6,9,11-trihydroxy-5,12-Napthacenedione, compound (8) is purified from said reaction mixture.

7. The method for synthesizing Annamycin of claim 5 wherein said (7S-cis)-7-[(2,6-dideoxy-2-iodo-α-L-mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione, compound (8) is purified from said reaction mixture by precipitation.

8. The method for synthesizing Annamycin of claim 1 wherein said produced Annamycin is a precipitate in said reaction mixture.

9. The method for synthesizing Annamycin of claim 1 wherein said Annamycin is further purified by at least two precipitation steps.

10. A method of synthesizing Annamycin consisting of:
  (a) reacting (7S-cis)-7-[(3,4-di-O-acetyl-2,6-dideoxy-2-iodo-β-L-glycopyranosyl)oxy]-9-[[[(1,1-dimethylethyl)dimethylsilyl]oxy]acetyl]-7,8,9,10-tetrahydro-6,9,11-trihydroxy-5,12-Napthacenedione compound (6) and (7S-cis)-7-[(3,4-di-O-acetyl-2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione compound (7) with sodium methoxide in a reaction that selectively deacylates (7S-cis)-7-[(3,4-di-O-acetyl-2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, compound (7) forming (7S-cis)-7-[(2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, compound (8), (b) purifying intermediate (7S-cis)-7-[(2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, (8), of FIG. 1 by precipitation, (c) mixing the filtered (7S-cis)-7-[(2,6-dideoxy-2-iodo-α-L-mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione, compound (8), with HCl, and (d) precipitating Annamycin from a solution of HCl and tetrahydrofuran.

11. An Annamycin/THF complex produced by the process comprising mixing (7S-cis)-7-[(2,6-dideoxy-2-iodo-"-L-mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione, compound (8), with the solvent tetrahydrofuran and an acid in a reaction mixture that desilylates (7S-cis)-7-[(2,6-dideoxy-2-iodo-"-L-mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione, compound (8).

12. The Annamycin/THF complex produced by the process of
  (a) reacting (7S-cis)-7-[(3,4-di-O-acetyl-2,6-dideoxy-2-iodo-β-L-glycopyranosyl)oxy]-9-[[[(1,1-dimethylethyl)dimethylsilyl]oxy]acetyl]-7,8,9,10-tetrahydro-6,9,11-trihydroxy-5,12-Napthacenedione compound (6) and (7S-cis)-7-[(3,4-di-O-acetyl-2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione compound (7) with sodium methoxide in a reaction that selectively deacylates (7S-cis)-7-[(3,4-di-O-acetyl-2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, compound (7) forming (7S-cis)-7-[(2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, compound (8), (b) purifying intermediate (7S-cis)-7-[(2,6-dideoxy-2-iodo-α-L-mannopyranosyl)oxy]-9-[[[(1,1-dimethylethyl)dimethylsilyl]oxy]acetyl]-7,8,9,10-tetrahydro-6,9,11-trihydroxy-5,12-Napthacenedione, (8), of FIG. 1 by precipitation, (c) mixing the filtered (7S-cis)-7-[(2,6-dideoxy-2-iodo-α-L-mannopyranosyl)oxy]-9-[[[(1,1-dimethylethyl) dimethylsilyl]oxy]acetyl]-7,8,9,10-tetrahydro-6,9,11-trihydroxy-5,12-Napthacenedione, compound (8), with HCl and tetrahydrofuran, and (d) precipitating Annamycin from a solution of HCl and tetrahydrofuran as an Annamycin/THF complex.

13. Annamycin/THF complex.

* * * * *